(12) United States Patent
Ruman et al.

(10) Patent No.: US 6,727,404 B2
(45) Date of Patent: Apr. 27, 2004

(54) DISPOSABLE ABSORBENT GARMENTS HAVING FLUID HANDLING CHARACTERISTICS THAT ENCOURAGE TOILET TRAINING

(75) Inventors: Marcille Faye Ruman, Neenah, WI (US); Lawrence Howell Sawyer, Neenah, WI (US); Christopher Peter Olson, Neenah, WI (US); Shirlee Ann Weber, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/293,886

(22) Filed: Nov. 12, 2002

(65) Prior Publication Data

US 2003/0125698 A1 Jul. 3, 2003

Related U.S. Application Data

(63) Continuation-in-part of application No. 10/025,173, filed on Dec. 19, 2001.

(51) Int. Cl.[7] ................................................ A61F 13/15
(52) U.S. Cl. .......................... 604/378; 604/385.101; 604/367
(58) Field of Search .................. 604/378, 385.101, 604/364, 365, 366, 367, 368, 372, 375, 377, 376; 442/218, 212, 416

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,340,563 A | 7/1982 | Appel et al. |
| 4,619,649 A | 10/1986 | Roberts |
| 4,663,220 A | 5/1987 | Wisneski et al. |
| 4,704,116 A | 11/1987 | Enloe |
| 4,940,464 A | 7/1990 | Van Gompel et al. |
| 5,046,272 A | 9/1991 | Vogt et al. |
| 5,061,259 A | 10/1991 | Goldman et al. |
| 5,062,839 A | 11/1991 | Anderson |
| 5,104,116 A | 4/1992 | Pohjola |
| 5,224,405 A | 7/1993 | Pohjola |
| 5,226,992 A | 7/1993 | Morman |
| 5,342,343 A | 8/1994 | Kitaoka et al. |
| 5,354,289 A | 10/1994 | Mitchell et al. |
| H1376 H | 11/1994 | Osborn, III et al. |
| 5,658,268 A | 8/1997 | Johns et al. |
| 5,728,082 A | 3/1998 | Gustafsson et al. |
| 5,797,892 A | 8/1998 | Glaug et al. |
| 5,820,973 A | * 10/1998 | Dodge et al. ................ 428/212 |
| 5,994,615 A | * 11/1999 | Dodge et al. ................ 604/378 |
| 6,152,904 A | * 11/2000 | Matthews et al. .......... 604/378 |
| 6,506,959 B2 | 1/2003 | Hamajima et al. |
| 2002/0156441 A1 | 10/2002 | Sawyer et al. |

FOREIGN PATENT DOCUMENTS

| | | |
|---|---|---|
| EP | 0 217 032 | 4/1987 |
| EP | 0 304 319 A2 | 2/1989 |
| GB | 2 063 683 A | 6/1981 |
| WO | WO 92/07534 | 5/1992 |
| WO | 94/10958 | 5/1994 |
| WO | 01/00117 | 1/2001 |
| WO | WO 01/34082 A1 | 5/2001 |

\* cited by examiner

*Primary Examiner*—Weilun Lo
*Assistant Examiner*—Jacqueline F Stephens
(74) *Attorney, Agent, or Firm*—Pauley Petersen & Erickson

(57) ABSTRACT

A disposable absorbent pant having fluid handling characteristics useful for encouraging toilet training. The pant has a limited absorbent capacity of between about 30 grams and about 400 grams, which contributes to a slow fluid intake, pooled fluid, and delayed fluid lock-up in the absorbent pad. The pant also has considerable fluid distribution, resulting in a large area of wetness. Each of these fluid handling characteristics provides awareness to a wearer of the filled status of the pant.

48 Claims, 6 Drawing Sheets

DISPOSABLE ABSORBENT GARMENTS HAVING FLUID HANDLING CHARACTERISTICS THAT ENCOURAGE TOILET TRAINING

CROSS-REFERENCE TO RELATED APPLICATION

This application is a continuation-in-part application of U.S. patent application Ser. No. 10/025,173 filed Dec. 19, 2001.

BACKGROUND OF THE INVENTION

This invention is directed to a disposable absorbent pant having fluid handling characteristics that encourage a wearer to progress through and complete the toilet training process.

When a child begins toilet training, the toilet training process may be hampered by the child's inability to discern the difference between diapers and training pants if the training pants are as thick and cumbersome as the diapers. If the training pants appear to be too diaper-like, the child may not be motivated to participate in the toilet training process. Furthermore, if the training pants absorb liquid rapidly, the toilet training process may be further hampered by the child's inability to sense wetness within the garment. Thin absorbents not only provide for a greater garment-like appearance and improved discretion when worn under other garments, but also may provide limited absorbent capacity that results in fluid handling characteristics that encourage children to complete the toilet training process at a faster rate than children wearing currently available disposable diapers and training pants.

During the toilet training process, a child may be particularly motivated to become fully toilet-trained if his or her training pants hold only a limited amount of waste. More particularly, if a training pant is designed to absorb multiple insults, the child may not be as aware of having urinated and may not be as motivated to change his or her training pant immediately after the first insult. However, if a training pant is designed to hold only one or two insults, and is further designed to handle the fluid in such a manner that the child is aware that fluid is present in the training pant, the child may be more likely to realize immediately after a first insult that a clean training pant should be applied in order to avoid any embarrassing leakage that would occur after multiple insults.

Leakage protection is very important in training pants designed to hold only one or two insults. If a training pant leaks with less than one insult or at very low volumes of urine, the child may become frustrated with toilet training. The child may perceive the act of changing the training pant as futile, since the garment is destined to leak regardless of the number or amount of insults. Furthermore, leakage protection in a training pant having limited absorbent capacity benefits the wearer by providing a safeguard against embarrassing leakage after a first insult, and also benefits a caregiver by preventing extra work and stains in the wearer's clothing if the wearer informs the caregiver of the need to change the training pant after the first insult. If the wearer of a training pant having limited absorbent capacity and leakage protection exceeds the capacity of the pant by issuing multiple insults, the wearer not only experiences unavoidable leakage due to the excessive urine volume but also incurs disappointment from the caregiver, thus giving the training pant wearer an incentive to become toilet trained. The wearer of a limited absorbent capacity training pant may be further motivated to become toilet trained through the realization of the hassle of having to have the pants changed after every insult.

There is a need or desire for a disposable absorbent pant that encourages accelerated toilet training.

There is a further need or desire for a low capacity disposable absorbent pant that is capable of absorbing only one or two insults, and preventing leakage of one or two insults, while providing awareness to the wearer of the wetness incurred from one or two insults.

SUMMARY OF THE INVENTION

In response to the discussed difficulties and problems encountered in the prior art, a low capacity disposable absorbent pant having fluid handling characteristics that encourage accelerated toilet training has been discovered.

The disposable absorbent pant includes a chassis with a waist opening and a pair of leg openings defined therein. The chassis includes an outer cover, a body side liner at least partially bonded to the outer cover, and an absorbent pad positioned between the outer cover and the body side liner. The absorbent article is designed to function over a wide range of user activities and positions while providing a thin, garment-like appearance.

The training pant including the thin absorbent pad looks more like "big kid" underwear than a bulky diaper, and is more discreet underneath clothing than a bulky diaper. The absorbent pad itself is suitably less than about 2 millimeters thick, and the entire absorbent article is suitably less than about 3 millimeters thick.

The low absorbent capacity and fluid handling characteristics of the absorbent article of the invention may motivate a child to change into a clean training pant immediately after issuing an insult into the training pant. More particularly, the pant suitably has an absorbent capacity of between about 30 and about 400 grams, or between about 40 and about 300 grams, or between about 50 and about 150 grams.

A slow fluid intake time results in pooled fluid, which can be felt by the wearer. Suitably, the pant has a fluid intake rate for a 40 milliliter (ml) insult of at least 7 seconds, or at least 12 seconds, or at least 16 seconds, and a fluid intake rate for an 80 ml insult of at least 45 seconds, or at least 65 seconds, or at least 80 seconds.

Also, a delayed fluid lock-up time, exemplified by an initially high fluid flowback followed by a much reduced fluid flowback, causes a squishy, uncomfortable feeling which also makes the wearer aware of the wetness within the pant. Suitably, the pant has a final flowback of a 40 ml insult of less than 35% of an initial flowback of the 40 ml insult, or a final flowback of the 40 ml insult of less than 30% of the initial flowback, or a final flowback of the 40 ml insult of less than 25% of the initial flowback, and a final flowback of an 80 ml insult of less than 60% of an initial flowback of the 80 ml insult, or a final flowback of the 80 ml insult of less than 50% of the initial flowback, or a final flowback of the 80 ml insult of less than 45% of the initial flowback.

Additionally, a fluid distribution covering a considerable portion of the absorbent pad means that the wetness can come into contact with a larger surface area of the wearer's skin to increase the wearer's ability to realize that he or she is wet. Suitably, the pant has a fluid distribution of an 80 ml insult of at least 60%, or at least 65%, or at least 70%.

A Cradle Test, described herein, can be used to measure the fluid handling characteristics of the absorbent pant of the invention, as well as the fluid handling characteristics of other absorbent pants for comparison purposes. From the data provided herein, it can be seen that an absorbent pant having the fluid handling characteristics described herein can be used to effectively toilet train a child. Training pants are often tested and found to have measurable differences compared to conventional training pants, but such differences are not necessarily felt by the wearer of the garment. However, the differences found in the garments of the present invention are measurable in terms of quantitative data as well as in qualitative differences experienced by the wearer. Recognizing and responding to urination are key accomplishments associated with toilet training progress and are taught by this pant.

With the foregoing in mind, particular embodiments of the invention provide an absorbent article that imparts wetness awareness in the garment.

Additionally, particular embodiments of the invention provide a method and a toilet training garment that motivate a child to complete the toilet training process more quickly than using conventional absorbent garments.

DEFINITIONS

Figure 1:
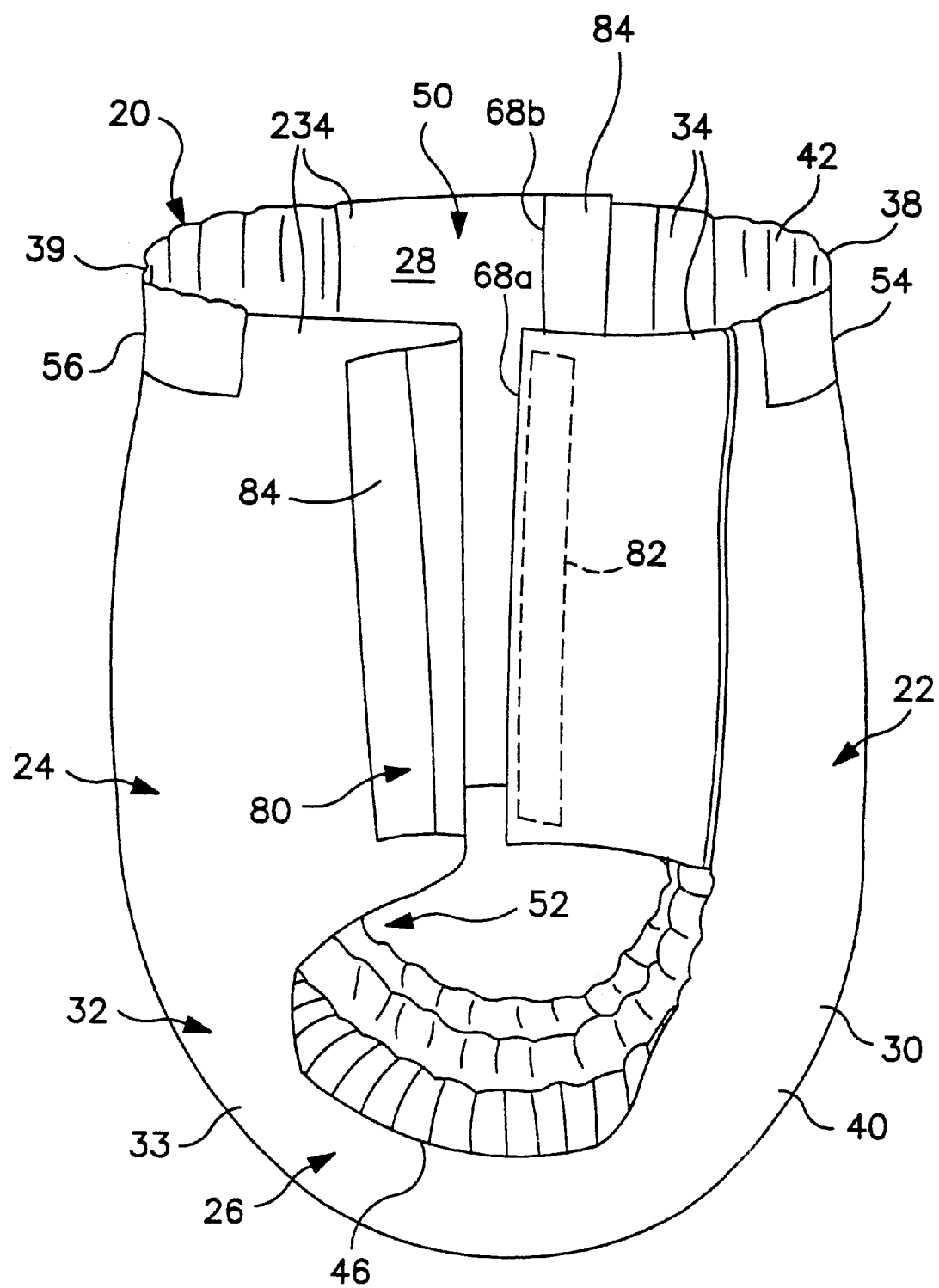
FIG. 1 is a side perspective view of an absorbent garment having a low capacity absorbent pad, according to one embodiment of this invention.

Within the context of this specification, each term or phrase below will include the following meaning or meanings.

"Absorbent capacity" refers to the maximum volume of liquid that can be absorbed by a product as measured by the Saturated Capacity Test.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Disposable" refers to garments or articles which are designed to be discarded after a limited use rather than being laundered or otherwise restored for reuse.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabric" is used to refer to all of the woven, knitted and nonwoven fibrous webs.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Flowback" refers to the amount of liquid released by a product under vacuum. As used herein, the term "initial flowback" refers to the flowback after 1 minute under vacuum, and the term "final flowback" refers to the flowback after 15 minutes under vacuum.

"Fluid distribution" refers to the percentage of a pad over which an insult is distributed, based on the maximum length of the pad over which the fluid is present in view of the overall length of the pad.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, while fibers having contact angles greater than 90 are designated "non-wettable" or hydrophobic.

"Insult liquid volume runoff" refers to the amount of liquid that exceeds the absorbent capacity, or saturated capacity, of a material in a target zone.

"Intake rate" refers to the length of time it takes for a product to absorb a set amount of liquid, including any standing liquid.

"Integral" or "integrally" is used to refer to various portions of a single unitary element rather than separate structures bonded to or placed with or placed near one another.

"Layer" when used in the singular can have the dual meaning of a single element or a plurality of elements (i.e., an element may consist of multiple layers).

"Liquid-impermeable," when used to describe a layer or laminate means that liquid such as urine will not pass through the layer or laminate under ordinary use conditions in a direction generally perpendicular to the plane of the layer or laminate at the point of liquid contact.

"Liquid-permeable," refers to a layer or laminate that is not liquid impermeable.

Figure 2:
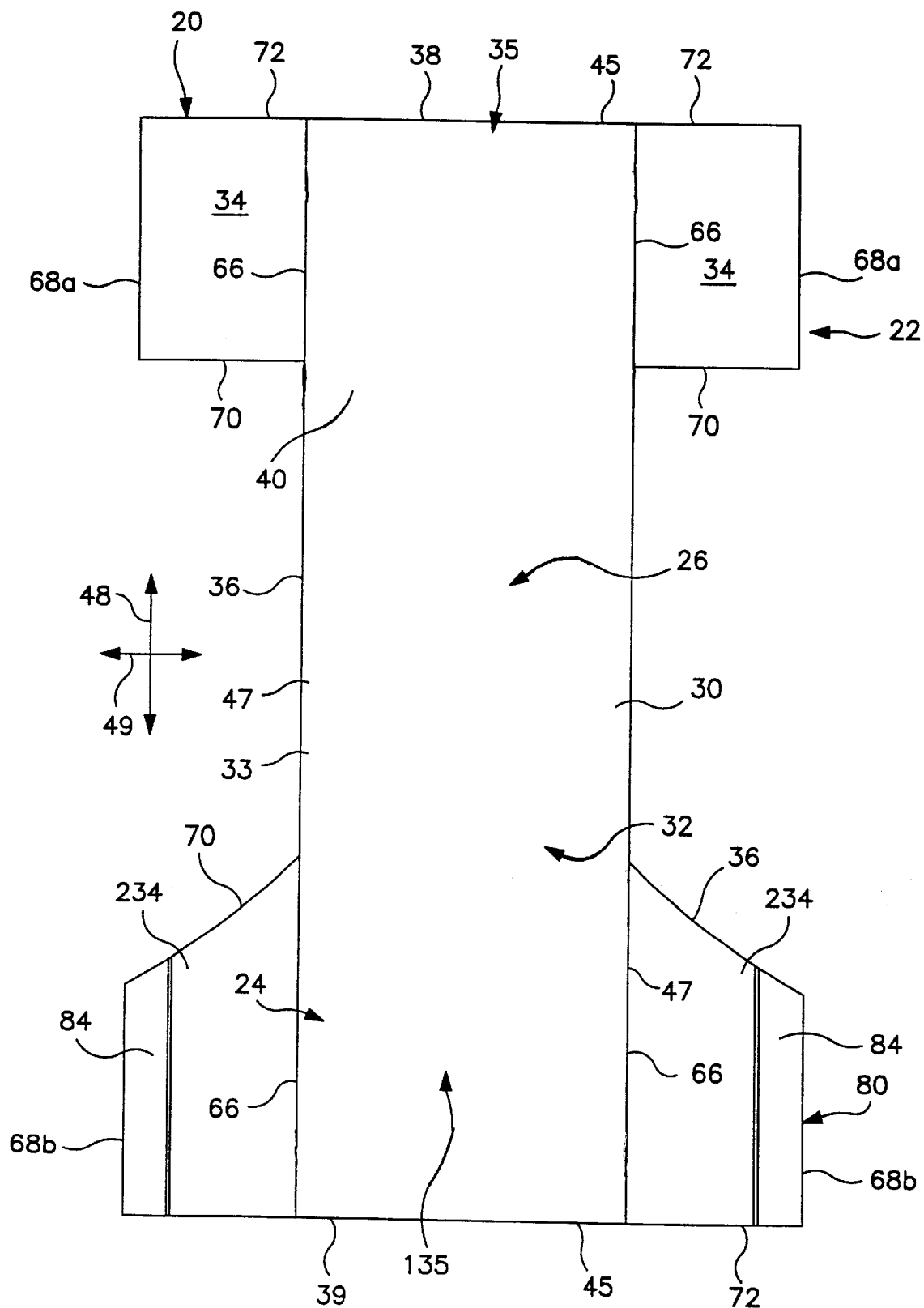
FIG. 2 is a plan view of the absorbent garment of FIG. 1 in a partially disassembled, stretched flat state, and showing the surface of the garment that faces away from the wearer when the garment is worn, according to one embodiment of this invention.
Figure 3:
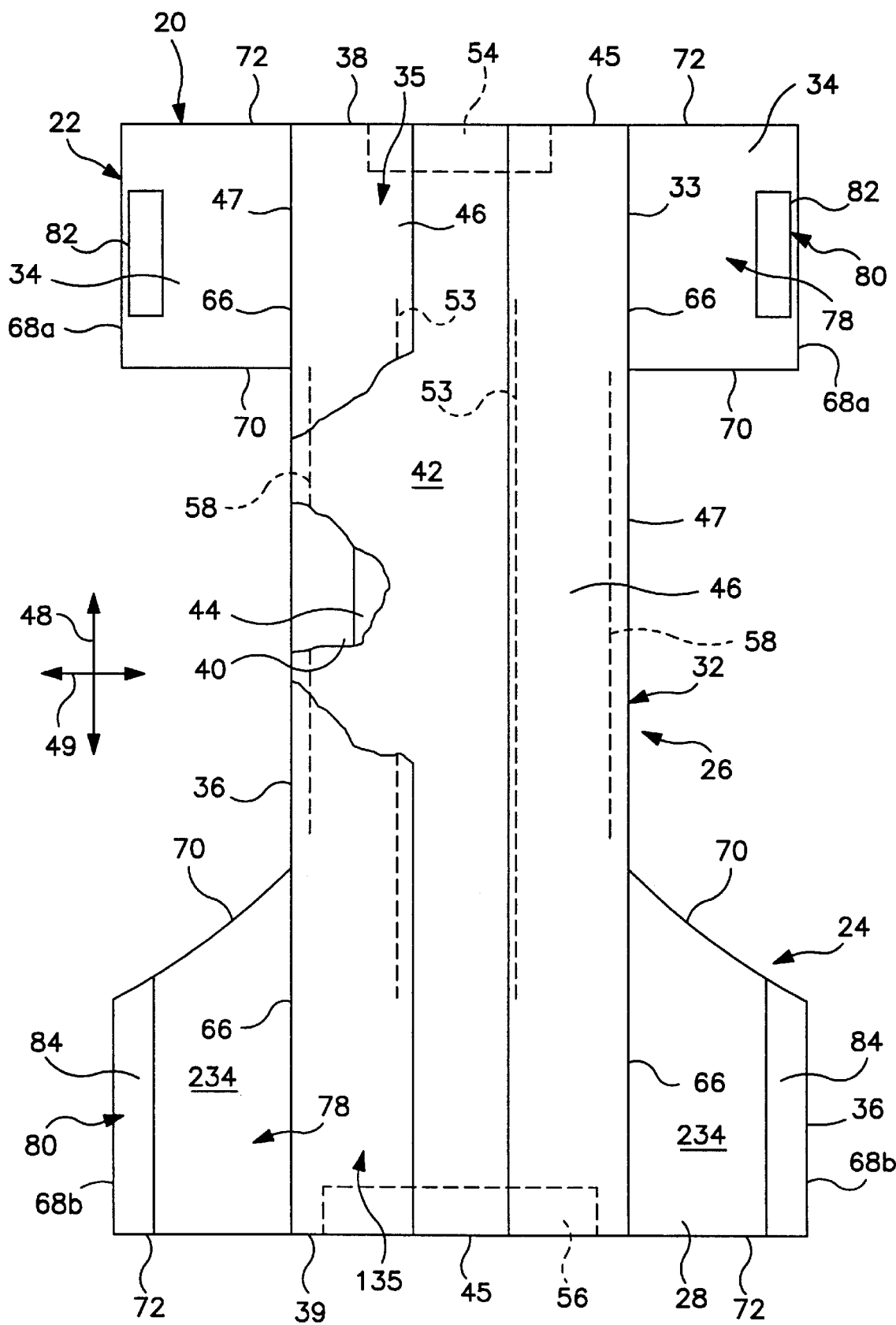
FIG. 3 is a plan view of the absorbent garment of FIGS. 1 and 2 in a partially disassembled, stretched flat state, and showing the surface of the garment that faces the wearer when the article is worn, and with portions cut away to show the underlying features, according to one embodiment of this invention.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joint or attachment. The joining, attaching, connecting or the like can be either directly, such as joining either member directly to an element, or can be indirectly by means of another member disposed between the first member and the first element.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Product thickness" refers to the caliper of the thickest portion of the open, laid flat product.

"Refastenable" refers to the property of two elements being capable of releasable attachment, separation, and subsequent releasable reattachment without substantial permanent deformation or rupture.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 1.2 times of its initial (unstretched) length in at least one direction.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

These terms may be defined with additional language in the remaining portions of the specification.

DESCRIPTION OF PREFERRED EMBODIMENTS

The present invention is directed to a disposable absorbent garment and a method of using such a garment to encourage a wearer, such as a child, to accelerate through the toilet training process. The garment has a limited absorbent capacity, with the ability to accommodate one or two insults with a low probability of leakage. When an insult is discharged into the garment, the fluid tends to temporarily form a pool in the garment, thus giving the wearer the sensation of liquid in contact with the wearer's skin. The fluid is slowly absorbed into the garment, providing enough contact time with the wearer's skin to make the wearer fully aware of the liquid. The fluid is absorbed and distributed across a considerable longitudinal length of the garment, with the large distribution area increasing the wearer's exposure to the wetness sensation.

Parents and other caregivers often cite noticeable feelings of wetness and feared leakage by the child as two factors that tend to accelerate a child's progress in the toilet training process. The pooled liquid, the slow intake time, and the large fluid distribution area of the garment of the present invention each contribute to noticeable feelings of wetness experienced by the wearer. The limited absorbent capacity of the garment of the invention is capable of maintaining one insult without leakage, but tends to leak if the wearer does not respond after the first insult and continues to issue multiple insults. Thus, the garment of the invention having such fluid handling characteristics can be used as an effective toilet training aid to accelerate toilet training as well as to achieve completion of toilet training.

More particularly, in one embodiment of the invention, the garment has an intake rate for a 40 milliliter insult of at least 7 seconds, or at least 12 seconds, or at least 16 seconds. For an 80 milliliter insult, the garment suitably has an intake rate of at least 45 seconds, or at least 65 seconds, or at least 80 seconds. The fluid intake rate can be measured using the Cradle Test, described in detail below. Example 1 compares the intake rates of several embodiments of the present invention and several commercially available products. Garments having a slow intake rate create a pooling effect in the garment, wherein the liquid sloshes around and makes contact with the wearer's skin before being absorbed. After the fluid intake is complete, the fluid is temporarily stored both in surge materials as well as fluff materials. During the fluid intake time, the fluff starts to wick the fluid away from the insult area and superabsorbent begins to desorb the fluff material. As the superabsorbent desorbs the fluff material, the superabsorbent locks up the fluid.

Although the intake rate is relatively slow, the liquid is eventually locked up. The liquid lock-up can be measured in terms of flowback using the Cradle Test. Thus, the flowback is relatively high at first, but after about 15 minutes is considerably lower, thereby allowing the liquid to contact the wearer's skin for a limited time which forces the wearer to sense the wetness, and then locking up the liquid to prevent it from spilling out of the pant when the pant is pulled down or removed. Locking up the fluid in the superabsorbent also decreases the possibility of skin irritation by distancing the fluid from the skin. More particularly, the garment suitably has a final flowback of a 40 milliliter insult of less than 35% of an initial flowback of the 40 milliliter insult, or less than 30%, or less than 25% of the initial flowback. For an 80 milliliter insult, the garment suitably has a final flowback of less than 60% of an initial flowback of the insult, or less than 50%, or less than 45% of the initial flowback.

If pressure, such as from the child sitting, pushing legs together, or grabbing the crotch area, is applied to the absorbent garment prior to fluid lock-up, the loose fluid in the absorbent pad will be released. The released fluid will again make contact with the child's skin.

In addition to the wetness, the absorbent pad feels very squishy and not firm until the fluid is locked up. This squishy feeling makes the absorbent pad more mobile and uncomfortable. Although this jelly-like feeling (supersaturated absorbent) could occur before the fluid intake is complete, it is probably most noticeable to the child after the fluid pooling disappears (upon intake) and before the fluid locks up. After the fluid is locked up, the absorbent pad feels thicker and stiffer.

Another characteristic of one embodiment of the absorbent pant of the invention, mentioned above, that promotes the feeling of wetness, thereby encouraging a wearer to accelerate through the toilet training process, is the considerably large fluid distribution. At least one embodiment of the garment of the invention uses over half the absorbent pad length, even at smaller insults such as 40 ml, to absorb the insult. More specifically, with an 80 ml insult, at least 60%, or at least 65%, or at least 70% of the length of the pad is used to distribute the insult. The fluid distribution can be determined using the Cradle Test, described below. With the insult being spread across so much of the absorbent pad, the wetness comes into contact with a considerable amount of surface area of the child's skin, making the child quite aware of the existing wetness.

Referring to FIG. 1, a disposable absorbent pant, such as a training pant 20, in accordance with one embodiment of the invention, is illustrated in a partially fastened condition. The training pant 20 includes a chassis 32 and a fastening system 80. The chassis 32 defines a front region 22, a back region 24, a crotch region 26 interconnecting the front and back regions, an inner surface 28 which is configured to contact the wearer, and an outer surface 30 opposite the inner surface which is configured to contact the wearer's clothing. As shown in further detail in FIGS. 2 and 3, the chassis 32 also defines a pair of transversely opposed side edges 36 and a pair of longitudinally opposed waist edges, which are designated front waist edge 38 and back waist edge 39. The front region 22 is contiguous with the front waist edge 38, and the back region 24 is contiguous with the back waist edge 39.

The illustrated chassis 32 includes a somewhat rectangular composite structure 33, a pair of transversely opposed front side panels 34, and a pair of transversely opposed back side panels 234. Alternatively, the absorbent composite can be shaped as, for example, an hourglass, with wider front and/or back sections. The composite structure 33 and side panels 34 and 234 may be integrally formed or may include two or more separate elements, as shown in FIGS. 2 and 3. The illustrated composite structure 33 includes an outer cover 40, a bodyside liner 42 which is connected to the outer cover in a superposed relation, and an absorbent pad 44 (FIG. 3) which is positioned or located between the outer cover 40 and the bodyside liner 42. The composite structure 33 may also include a pair of containment flaps 46, as shown in FIG. 3. A surge material may be positioned between the absorbent pad and body side liner 42. The absorbent composite structure 33 has opposite linear end edges 45 that form portions of the front and back waist edges 38 and 39, and opposite linear side edges 47 that form portions of the side edges 36 of the chassis 32 (FIGS. 2 and 3). For reference, arrows 48 and 49 depicting the orientation of the longitudinal axis and the transverse axis, respectively, of the training pant 20 are illustrated in FIGS. 2 and 3.

With the training pant 20 in the fastened position as partially illustrated in FIG. 1, the front and back regions 22 and 24 are joined together to define a three-dimensional pant configuration having a waist opening 50 and a pair of leg openings 52. The front region 22 includes the portion of the training pant 20 which, when worn, is positioned on the front of the wearer while the back region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer. The front and back side panels 34 and 234 include the portions of the training pant 20 which, when worn, are positioned on the hips of the wearer.

The front region 22 of the chassis 32 includes the transversely opposed front side panels 34 and a front center panel 35 (FIGS. 2 and 3) positioned between and interconnecting the side panels, along with a front waist elastic member 54 and any other connected components. The back region 24 of the chassis 32 includes the transversely opposed back side panels 234 and a back center panel 135 (FIGS. 2 and 3) positioned between and interconnecting the side panels, as well as a rear waist elastic member 56 and any other connected components. The waist edges 38 and 39 of the chassis 32 are configured to encircle the waist of the wearer when worn and provide the waist opening 50 which defines a waist perimeter dimension. Portions of the transversely opposed side edges 36 in the crotch region 26 generally define the leg openings 52.

The chassis 32 is configured to contain and/or absorb any body exudates discharged from the wearer. Any of a number of devices used to forestall leakage around the leg openings may be included in certain embodiments of the garment of the invention. For example, the chassis 32 desirably, although not necessarily, may include the pair of containment flaps 46 which are configured to provide a barrier to the transverse flow of body exudates. A flap elastic member 53 (FIG. 3) is operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the chassis 32, and can extend longitudinally along the entire length of the chassis or may only extend partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

Another type of device that may be used to forestall leakage is elastic leg cuffs (not shown). Leg cuffs can be made of elastic stretch-bonded laminate material or any other suitable elastomeric materials. Leg cuffs can be attached around the leg openings 52 between the front and back side panels 34, 234. The leg cuffs can be wholly attached to the outer cover 40 or to the bodyside liner 42. In one embodiment, leg cuffs can be wrapped around from the outer cover 40 to the bodyside liner 42 forming a hem-like leg band. In another embodiment, leg cuffs can be partially attached to the outer cover 40 or bodyside liner 42 so that the leg cuffs overhang. Leg cuffs can be attached under tension so that they gather in the chassis 32 when the tension is released. In yet another embodiment, leg cuffs can be heat shrinkable so that they gather in the leg edge of the chassis 32 when heat activated.

To further enhance containment and/or absorption of body exudates, the training pant 20 desirably includes the front waist elastic member 54, the rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38 and 39, and can extend over part or all of the waist edges. The leg elastic members 58 are desirably operatively joined to the outer cover 40 and/or bodyside liner 42 along the opposite side edges 36 and positioned in the crotch region 26 of the training pant 20. The leg elastic members 58 are desirably longitudinally aligned along each side edge 47 of the composite structure 33.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 include a plurality of dry-spun coalesced multifilament spandex elastomeric threads sold under the trade name LYCRA® and available from E. I. DuPont de Nemours and Company, Wilmington, Del., U.S.A.

The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.2 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

The liquid permeable bodyside liner 42 is illustrated as overlying the outer cover 40 and absorbent pad 44, and may but need not have the same dimensions as the outer cover 40. The bodyside liner 42 is desirably compliant, soft feeling, and non-irritating to the wearer's skin. Further, the bodyside liner 42 can be less hydrophilic than the absorbent pad 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 from Hodgson Textile Chemicals of Mount Holly, N.C., U.S.A. and GLUCOPON® 220UP from Henkel Corporation of Ambler, Pa., in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can include elastomeric materials, it can be desirable in some embodiments for the composite structure to be generally inelastic, where the outer cover, the bodyside liner and the absorbent pad include materials that are generally not elastomeric.

In accordance with one embodiment of this invention, the absorbent pad 44, as shown in FIG. 3, is positioned or located between the outer cover 40 and the bodyside liner 42, which components can be joined together by any suitable means, such as adhesives, as are well known in the art. The absorbent pad 44 is thin, flexible, and has a low mass, thus maximizing fit and comfort when dry, and resulting in some discomfort when wet. The term "low mass" refers to a total product weight of less than 30 grams or less than 25 grams or less than 20 grams for pants intended for use on children of 20 to 50 pounds.

The absorbent pad 44 suitably has a thickness of less than about 2 millimeters (mm), or less than about 1.5 mm, or, as another alternative, less than about 1 mm. The training pant 20 suitably has a combined thickness of all of its layers, including the outer cover 40, the absorbent pad 44, and the body side liner 42, of less than about 3 mm, or less than about 2.5 mm, or, alternatively, less than about 2 mm. The thickness of the absorbent pad 44 as well as the combined thickness of all layers, can be calculated according to the Bulk and Density Testing, described below.

Absorbent capacity of the absorbent article 20 is based on the anticipated insult volume of a single void. The absorbent capacity of the garment 20 can be adjusted to accommodate insults across a wide range of user positions, including standing, sitting and prone. For example, the capacity can be adjusted by zoning greater amounts of superabsorbent in certain areas of the pad 44 and lesser amounts of superabsorbent in other areas of the pad 44 and/or layering the superabsorbent, and/or using different types of superabsorbent in different locations in the absorbent structure.

The absorbent capacity, as determined by 0.5 psi saturation capacity (test method described below), is suitably no more than three times the anticipated single insult size, or no more than twice the anticipated single insult size, or approximately 90–150% of the anticipated single insult size. For example, absorbent articles 20 can be designed and produced to accommodate children between about 18 months and about 60 months old, with insult volumes from 30 ml to 180 ml, or from less than 50 ml to 150 ml, and higher if necessary. Anticipated single void insult size is typically less than 60 ml but can be greater than 100 ml.

The overall absorbent capacity of the absorbent pad 44 is expressed in terms of grams (g) of fluid absorbed (and retained). The overall absorbent capacity of the absorbent pad 44 is suitably not greater than about three times an anticipated insult volume, or not greater than about two times an anticipated insult volume, and thus is desirably capable of accommodating an insult having a volume of about 30 grams (g) to about 400 g, or desirably about 40 g to about 300 g, or about 50 g to about 150 g. The saturated capacity (i.e. absorbent efficiency) of the absorbent pad 44 is expressed in terms of grams (g) of fluid retained per gram (g) of absorbent structure, wherein a higher value represents a greater efficiency. The saturated capacity of the absorbent pad 44 is suitably greater than about 7 g/g, or about 9 g/g to about 11 g/g, or, alternatively, greater than about 12.0 g/g. Both overall absorbent capacity and saturated capacity of the absorbent pad 44 are determined by a saturated capacity test, described below.

This absorbent article capacity and product design provides better leakage performance than cloth training pants or underwear, with low leakage probabilities for insults below the anticipated single void volume. When leaks do occur, the severity of the leak is kept at a manageable level. For example, the absorbent article may experience less than 15%, or less than 10%, of insult liquid volume runoff when the product is insulted with volumes up to the target void volume, or anticipated insult volume. Leakage performance of the product is enhanced by the containment flaps 46 and the leg elastics 58.

An absorbent pad 44 including a fluff pulp and superabsorbent material, for example, possibly in combination with other components, is able to retain a specific amount of fluid that is determined by the individual fluid capacities of the components and their relative percentages within the absorbent structure 44. The superabsorbent material, or superabsorbent polymer (SAP), is highly efficient, whereas the fluff pulp material is moderately efficient. Synthetic fibers, such as polyester fibers, are generally very inefficient. An "efficient" absorbent structure will retain a relatively large volume of fluid, whereas an "inefficient" absorbent structure will retain a relatively small volume of fluid.

The absorbent pad 44 can be any structure which is generally compressible, conformable, non-irritating to the wearer's skin, and capable of absorbing and retaining liquids and certain body wastes at the levels discussed herein. The absorbent pad 44 can be manufactured in a wide variety of sizes and shapes, and from a wide variety of liquid absorbent materials commonly used in the art. For example, the absorbent pad 44 can suitably include a matrix of hydrophilic fibers, such as a web of cellulosic fluff, mixed with particles of a high-absorbency material commonly known as superabsorbent material. In a particular embodiment, the absorbent pad 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent pad 44 to better contain and absorb body exudates. The concentration of the superabsorbent particles can also vary through the thickness of the absorbent pad 44. Alternatively, the absorbent pad 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

More particularly, the absorbent pad 44 can include an extremely thin absorbent composite material sold under the trade name NOVATHIN® available from EAM Corporation located in Jessup, Ga., U.S.A., and/or an ultra-thin-absorbent (UTA) material including a mixture of SAP and pulp fiber. An example of a suitable UTA may include 3.7 grams (g) of FAVOR® SXM 9543 SAP, available from Stockhausen GmbH & Co. KG located in Krefeld, Fed. Rep. of Germany, and 3.7 g of NB416 pulp fiber available from Weyerhauser located in Federal Way, Wash.

In one embodiment, the absorbent pad 44 can be generally rectangular in shape, and can include a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent pad 44 in an amount of from about 5 to about 90 weight percent based on total weight of the absorbent pad 44. The absorbent pad 44 suitably has a density within the range of about 0.10 to about 0.50 grams per cubic centimeter. The absorbent pad 44 may or may not be wrapped or encompassed by a suitable tissue wrap that maintains the integrity and/or shape of the absorbent pad 44.

The chassis 32 can also incorporate other materials that are designed primarily to receive, temporarily store, and/or transport liquid along the mutually facing surface with the absorbent pad 44, thereby maximizing the overall absorbent capacity of the absorbent pad 44, if desired. One suitable material is referred to as a surge layer (not shown) and includes a material having a basis weight of about 50 to about 120 grams per square meter (gsm), and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A. Another example of a suitable surge layer may include a material made of 6 denier polyethylene terephthalate (PET) and 6 denier bicomponent binder fiber, having a basis weight of about 50 to about 120 gsm.

As noted previously, the illustrated training pant 20 has front and back side panels 34 and 234 disposed on each side of the chassis 32. These transversely opposed front side panels 34 and transversely opposed back side panels 234 can be permanently bonded to the composite structure 33 of the chassis 32 in the respective front and back regions 22 and 24, and can be releasably attached to one another by a fastening system 80. Alternatively, instead of being releasably attachable, the front and back side panels 34, 234 can be permanently bonded to one another, respectively, to create a pull-on pant.

As shown best in FIGS. 2 and 3, the front side panels 34 can be permanently bonded to and extend transversely beyond the linear side edges 47 of the composite structure 33 in the front region 22 along attachment lines 66, and the back side panels 234 can be permanently bonded to and extend transversely beyond the linear side edges of the composite structure in the back region 24 along attachment lines 66. The side panels 34 and 234 may be attached using attachment means known to those skilled in the art such as adhesive, thermal or ultrasonic bonding. The side panels 34 and 234 can also be formed as a portion of a component of the composite structure 33, such as the outer cover 40 or the bodyside liner 42.

In particular embodiments for improved fit and appearance, the side panels 34 and 234 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 234 desirably have an average length dimension of about 10 centimeters or greater, such as about 15 centimeters. While each of the side panels 34 and 234 extend from the waist opening 50 to one of the leg openings 52, the back side panels 234 have a continually decreasing length dimension moving from the attachment line 66 to a distal edge 68b of the back panel 234, as is best shown in FIGS. 2 and 3.

The side panels 34 and 234 desirably include an elastic material capable of stretching in a direction generally parallel to the transverse axis 49 of the training pant 20. Suitable elastic materials, as well as one described process of incorporating elastic side panels into a training pant, are known to those skilled in the art, and are described, for example, in U.S. Pat. No. 4,940,464 issued Jul. 10, 1990 to Van Gompel et al., which is incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art. Alternatively, the side panel material may include other woven or nonwoven materials, such as those described above as being suitable for the outer cover 40 or bodyside liner 42, or stretchable but inelastic materials.

As mentioned, the training pant 20 according to one embodiment of the present invention may include a fastening system 80 for securing the training pant about the waist of the wearer (FIG. 1). The illustrated fastening system 80 may include fastening components 82 that are adapted to refastenably connect to mating fastening components 84. The fastening system 80 may be refastenable or non-refastenable. In one embodiment, one surface of each of the fastening components 82 and 84 includes a plurality of engaging elements that project from that surface. The engaging elements of these fastening components 82 are adapted to repeatedly engage and disengage the engaging elements of the mating fastening components 84.

In one particular embodiment, the fastening components 82 each include hook type fasteners and the mating fastening components 84 each include complementary loop type fasteners. In another particular embodiment, the fastening components 82 each include loop type fasteners and the mating fastening components 84 each include complementary hook type fasteners. Alternatively, other types of fastening components, such as tapes, adhesives, cohesives, self-engaging fasteners, or other types of mechanical fasteners, can also be used.

Loop type fasteners typically include a fabric or material having a structure and a plurality of loop members on at least one surface of the structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. In one embodiment, the outer cover material and/or the body side liner material and/or the side panel material may serve as a loop type fastener, thus requiring no separately attached loop type fasteners. Loop materials can also be made up of any fibrous structure capable of entangling or catching hook materials, such as carded, spunbonded, or other nonwoven webs or composites, including elastomeric and nonelastomeric composites.

Hook type fasteners typically include a fabric or material having a plurality of hook members extending upwardly from at least one surface of the backing structure. Suitable single-sided hook materials for the fastening components 82 or the mating fastening components 84 are available from Velcro Industries B.V., Amsterdam, Netherlands or affiliates thereof. In one embodiment, the outer cover material and/or the body side liner material and/or the side panel material may serve as a hook type fastener.

As described herein, the various components of the absorbent garment 20 can be integrally assembled together employing various types of suitable attachment means, such as adhesive, sonic and thermal bonds or combinations thereof. The resulting product is an absorbent article having cloth-like thinness, low absorbent capacity, and which also provides leakage protection.

The present invention also includes a method of using the absorbent garment described herein to toilet train a child. The method includes donning the child in the absorbent garment and letting the fluid handling characteristics of the garment encourage the child to learn to identify wetness when an insult occurs, with the realization that multiple insults will result in embarrassing leakage, such that the child shall accelerate through and complete the toilet training process.

EXAMPLES

The following examples illustrate the differences in intake rates, fluid flowback, fluid distribution, and absorbent capacity among the garments of the invention compared to commercially available garments.

TABLE 1

Products Tested in Examples 1–4

| Product | Weight Range (lbs) | Absorbent Capacity (grams) | Super-absorbent/ Fluff (g/g) |
|---|---|---|---|
| Sample 1 (Boy) | 28–48 | 160 | 3.9/3.9 |
| Sample 2 (Girl) | 28–48 | 173 | 3.9/3.9 |
| Sample 3 (Boy) | 28–48 | 168 | 3.9/3.9 |
| Sample 4 (Boy) | 28–48 | 163 | 3.9/3.9 |
| Sample 5 (Boy) | 28–48 | 171 | 3.9/3.9 |
| Kao Torepants—Unisex | 26+ | 250 | 4.49/6.45 |
| UNICHARM Torepan Man—Boy | 20–31 | 133 | 1.15/7.23 |
| UNICHARM Torepan Man—Girl | 20–31 | 125 | 1.34/8.05 |
| HUGGIES PULL-UPS Disposable Training Pants, commercially available between about April 2002 and September 2002—Boy | 32–40 | 419 | 13.2/10.5 |
| HUGGIES PULL-UPS Disposable Training Pants, commercially available between about April 2002 and September 2002—Girl | 32–40 | 403 | 12.6/10.5 |
| HUGGIES PULL-UPS Disposable Training Pants, commercially available between about July 2001 and April 2002—Boy | 32–40 | 510 | 12.0/14.5 |
| HUGGIES Supreme Disposable Diapers—Unisex | 27+ | 525 | 13.3/18.0 |
| HUGGIES Ultratrim Disposable Diapers—Unisex | 27+ | 561 | 13.8/18.0 |
| PAMPERS EASY UPS—Unisex | 30–40 | 520 | 13.3/13.17 |
| New & Improved PAMPERS EASY UPS—Unisex | 30–40 | 495 | 12.81/13.38 |
| PARAGON White Cloud—Boy | 32–40 | 449 | 14.36/14.42 |
| PARAGON White Cloud—Girl | 32–40 | 482 | 14.16/15.06 |
| MERRIES Slender Fit—Unisex | 26+ | 562 | 11.25/10.71 |
| HUGGIES LITTLE SWIMMERS Disposable Swimpants—Unisex | 32–42 | 91 | 0/11.79 (coform) |
| LUVS SPLASHWEAR—Unisex | 32+ | 109 | 0/11.68 (coform) |
| Early Trainer Vinyl & Cloth Training Pant—Unisex (size 4) | 35+ | 190 | n/a |
| GERBER Cloth Training Pants—Unisex (size 4) | 33–38 | 188 | n/a |
| HANES Cloth Underwear—Boy (size 4) | 33–38 | 79 | n/a |
| HANES Cloth Underwear—Girl (size 4) | 28–38 | 58 | n/a |

TABLE 2

Product Descriptions of Samples 1–5

| Sample | Description |
|---|---|
| 1 | Absorbent pad: 3.9 g Dow DRYTECH 2035 superabsorbent, 3.9 g Weyerhaeuser ND 416 pulp, pad length 384 mm, width at front 100 mm, with cellulose tissue wrap sheet<br>Surge: 1.5 osy through-air bonded-carded web, surge length 254 mm placed 38 mm from front of pad<br>Outer cover: poly, 0.6 osy cloth, 6.75 inches wide<br>Body side liner: 5 inches wide, 0.06 osy, Ahcovel zone treated 0.45%<br>Side panels: 96 mm wide, 127 mm front length, continuous filament stretch-bonded laminate, 240% stretch-to-stop<br>Elastics: 2 strands leg elastic per side at 300% elongation, waist elastic<br>Containment flaps: 0.5 osy cloth 6 inches wide, 0.5 mil poly 4.8 inches wide, 3 strands elastic per flap at 300% elongation, flaps attached 70 mm from front of product, 110 mm from back of product, flap height 26 mm<br>Product thickness = 2.8 mm (front), 2.8 mm (back) |
| 2 | Absorbent pad: 3.9 g Dow DRYTECH 2035 superabsorbent, 3.9 g Weyerhaeuser ND 416 pulp, pad length 384 mm, width at front 100 mm, with cellulose tissue wrap sheet<br>Surge: 1.5 osy through-air bonded-carded web, surge length 254 mm placed 60 mm from front of pad<br>Outer cover: poly, 0.6 osy cloth, 6.75 inches wide<br>Body side liner: 5 inches wide, 0.06 osy, Ahcovel zone treated 0.45%<br>Side panels: 96 mm wide, 127 mm front length, continuous filament stretch-bonded laminate, 240% stretch-to-stop<br>Elastics: 2 strands leg elastic per side at 300% elongation, waist elastic<br>Containment flaps: 0.5 osy cloth 6 inches wide, 0.5 mil poly 4.8 inches wide, 3 strands elastic per flap at 300% elongation, flaps attached 70 mm from front of product, 110 mm from back of product, flap height 26 mm<br>Product thickness = 2.8 mm (front), 2.8 mm (back) |
| 3 | Absorbent pad: 3.9 g Dow DRYTECH 2035 superabsorbent, 3.9 g Weyerhaeuser ND 416 pulp, pad length 384 mm, width at front 100 mm, with cellulose tissue wrap sheet<br>Surge: 1.5 osy through-air bonded-carded web, surge length 254 mm placed 38 mm from front of pad<br>Outer cover: poly, 0.6 osy cloth, 6.75 inches wide |

TABLE 2-continued

Product Descriptions of Samples 1–5

| Sample | Description |
|---|---|
|  | Body side liner: 5 inches wide, 0.06 osy, Ahcovel zone treated 0.45% |
|  | Side panels: 96 mm wide, 127 mm front length, continuous filament stretch-bonded laminate, 240% stretch-to-stop |
|  | Elastics: 2 strands leg elastic per side at 300% elongation, waist elastic |
|  | Containment flaps: 0.6 osy spunbond-meltblown-spunbond, 0.5 mil poly 4.8 inches wide, 3 strands elastic per flap at 300% elongation, flaps attached 70 mm from front of product, 110 mm from back of product, flap height 26 mm |
|  | Product thickness = 2.8 mm (front), 2.8 mm (back) |
| 4 | Absorbent pad: 3.9 g Dow DRYTECH 2035 superabsorbent, 3.9 g Weyerhaeuser ND 416 pulp, pad length 384 mm, width at front 100 mm, with cellulose tissue wrap sheet |
|  | No Surge |
|  | Outer cover: poly, 0.6 osy cloth, 6.75 inches wide |
|  | Body side liner: 5-inches wide, 0.06 osy, Ahcovel zone treated 0.45% |
|  | Side panels: 96 mm wide, 127 mm front length, continuous filament stretch-bonded laminate, 240% stretch-to-stop |
|  | Elastics: 2 strands leg elastic per side at 300% elongation, waist elastic |
|  | Containment flaps: 0.5 osy cloth 6 inches wide, 0.5 mil poly 4.8 inches wide, 3 strands elastic per flap at 300% elongation, flaps attached 70 mm from front of product, 110 mm from back of product, flap height 26 mm |
|  | Product thickness = 2.8 mm (front), 2.8 mm (back) |
| 5 | Absorbent pad: 3.9 g Dow DRYTECH 2035 superabsorbent, 3.9 g Weyerhaeuser ND 416 pulp, pad length 384 mm, width at front 100 mm, with cellulose tissue wrap sheet |
|  | Surge: 1.5 osy through-air bonded-carded web, surge length 254 mm placed 38 mm from front of pad |
|  | Outer cover: poly, 0.6 osy cloth, 6.75 inches wide |
|  | Body side liner: 2 layers of 5-inch, 0.06 osy, Ahcovel zone treated 0.45% |
|  | Side panels: 96 mm wide, 127 mm front length, continuous filament stretch-bonded laminate, 240% stretch-to-stop |
|  | Elastics: 2 strands leg elastic per side at 300% elongation, waist elastic |
|  | Containment flaps: 0.5 osy cloth 6 inches wide, 0.5 mil poly 4.8 inches wide, 3 strands elastic per flap at 300% elongation, flaps attached 70 mm from front of product, 110 mm from back of product, flap height 26 mm |
|  | Product thickness = 2.8 mm (front), 2.8 mm (back) |

Example 1

Intake Rates

In this example, intake rates of the products shown in Table 1 were tested with both 40 ml insults and with 80 ml insults, using the Cradle Test. The results are shown in Table 3.

TABLE 3

Intake Rates

| Product | Intake Time (seconds) for 40 ml Insult | Intake Time (seconds) for 80 ml Insult |
|---|---|---|
| Sample 1 (Boy) | 24 | 92 |
| Sample 2 (Girl) | 19 | 84 |
| Sample 3 (Boy) | 19 | 89 |
| Sample 4 (Boy) | 27 | 102 |
| Sample 5 (Boy) | 15 | 76 |
| Kao Torepants—Unisex | 4 | 9 |
| UNICHARM Torepan Man—Boy | 5 | 43 |
| UNICHARM Torepan Man—Girl | 5 | 55 |
| HUGGIES PULL-UPS Disposable Training Pants, commercially available between about April 2002 and September 2002—Boy | 6 | 13 |
| HUGGIES PULL-UPS Disposable Training Pants, commercially available between about April 2002 and September 2002—Girl | 5 | 13 |
| HUGGIES PULL-UPS Disposable Training Pants, commercially available between about July 2001 and April 2002—Boy | 4 | 7 |
| HUGGIES Supreme Disposable Diapers—Unisex | 4 | 7 |
| HUGGIES Ultratrim Disposable Diapers—Unisex | 5 | 9 |
| PAMPERS EASY UPS—Unisex | 4 | 7 |
| New & Improved PAMPERS EASY UPS—Unisex | 4 | 7 |
| PARAGON White Cloud—Boy | 4 | 7 |
| PARAGON White Cloud—Girl | 4 | 8 |
| MERRIES Slender Fit—Unisex | 4 | 7 |
| HUGGIES LITTLE SWIMMERS Disposable Swimpants—Unisex | 7 | 965 |
| LUVS SPLASHWEAR—Unisex | 5 | 212 |
| Early Trainer Vinyl & Cloth Training Pant—Unisex (size 4) | 5 | 1172 |
| GERBER Cloth Training Pants—Unisex (size 4) | 7 | 7 |
| HANES Cloth Underwear—Boy (size 4) | 5 | n/a |
| HANES Cloth Underwear—Girl (size 4) | 8 | n/a |

Samples 1–5 and the HUGGIES LITTLE SWIMMERS Disposable Swimpants each exhibited pooling, or a puddle of initially unabsorbed liquid, which creates the desired "slosh factor" to aid in toilet training. A wearer most likely can feel the pool of fluid moving as the wearer moves.

Example 2

Fluid Flowback

In this example, fluid flowback of the products shown in Table 1 were tested at 1 minute (initial flowback) and again at 15 minutes (final flowback), using the Cradle Test. The results, including the percentage difference between the initial and final flowback, are shown in Table 4 (40 ml insult) and Table 5 (80 ml insult).

TABLE 4

Fluid Flowback (40 ml Insult)

| Product | Initial Flowback (grams) | Final Flowback (grams) | Final Flowback as a Percentage of Initial Flowback |
|---|---|---|---|
| Sample 1 (Boy) | 0.87 | 0.21 | 24% |
| Sample 2 (Girl) | 1.02 | 0.21 | 21% |
| Sample 3 (Boy) | 1.28 | 0.16 | 13% |
| Sample 4 (Boy) | 1.97 | 0.12 | 6% |
| Sample 5 (Boy) | 1.36 | 0.22 | 16% |
| Kao Torepants—Unisex | 0.14 | 0.14 | 100% |
| UNICHARM Torepan Man—Boy | 7.03 | 5.13 | 73% |
| UNICHARM Torepan Man—Girl | 7.90 | 6.04 | 76% |
| HUGGIES PULL-UPS Disposable Training Pants, commercially available between about April 2002 and September 2002—Boy | 0.25 | 0.16 | 64% |
| HUGGIES PULL-UPS Disposable Training Pants, commercially available between about April 2002 and | 0.25 | 0.15 | 60% |

TABLE 4-continued

Fluid Flowback (40 ml Insult)

| Product | Initial Flowback (grams) | Final Flowback (grams) | Final Flowback as a Percentage of Initial Flowback |
|---|---|---|---|
| September 2002—Girl | | | |
| HUGGIES PULL-UPS Disposable Training Pants, commercially available between July 2001 and April 2002—Boy | 0.13 | 0.09 | 69% |
| HUGGIES Supreme Disposable Diapers—Unisex | 0.28 | 0.11 | 39% |
| HUGGIES Ultratrim Disposable Diapers—Unisex | 0.17 | 0.10 | 59% |
| PAMPERS EASY UPS—Unisex | 0.06 | 0.10 | 167% |
| New & Improved PAMPERS EASY UPS—Unisex | 0.09 | 0.07 | 78% |
| PARAGON White Cloud—Boy | 0.19 | 0.21 | 111% |
| PARAGON White Cloud—Girl | 0.27 | 0.17 | 63% |
| MERRIES Slender Fit—Unisex | 0.12 | 0.11 | 92% |
| HUGGIES LITTLE SWIMMERS Disposable Swimpants—Unisex | 8.34 | 7.53 | 90% |
| LUVS SPLASHWEAR—Unisex | 7.04 | 6.57 | 93% |
| Early Trainer Vinyl & Cloth Training Pant—Unisex (size 4) | 12.71 | 12.18 | 96% |
| GERBER Cloth Training Pants—Unisex (size 4) | 7.86 | 7.48 | 95% |
| HANES Cloth Underwear—Boy (size 4) | 5.66 | 3.66 | 65% |
| HANES Cloth Underwear—Girl (size 4) | 4.17 | 3.21 | 77% |

TABLE 5

Fluid Flowback (80 ml Insult)

| Product | Initial Flowback (grams) | Final Flowback (grams) | Final Flowback as a Percentage of Initial Flowback |
|---|---|---|---|
| Sample 1 (Boy) | 10.66 | 3.65 | 34% |
| Sample 2 (Girl) | 10.26 | 3.76 | 37% |
| Sample 3 (Boy) | 10.44 | 3.78 | 36% |
| Sample 4 (Boy) | 11.85 | 4.91 | 41% |
| Sample 5 (Boy) | 10.63 | 6.22 | 59% |
| Kao Torepants—Unisex | 5.42 | 0.19 | 4% |
| UNICHARM Torepan Man—Boy | 15.89 | 14.54 | 92% |
| UNICHARM Torepan Man—Girl | 16.14 | 15.12 | 94% |
| HUGGIES PULL-UPS Disposable Training Pants, commercially available between about April 2002 and September 2002—Boy | 0.28 | 0.24 | 86% |
| HUGGIES PULL-UPS Disposable Training Pants, commercially available between about April 2002 and September 2002—Girl | 0.32 | 0.23 | 72% |
| HUGGIES PULL-UPS Disposable Training Pants, commercially available between about July 2001 and April 2002—Boy | 0.25 | 0.15 | 60% |
| HUGGIES Supreme Disposable Diapers—Unisex | 0.38 | 0.12 | 32% |
| HUGGIES Ultratrim Disposable Diapers—Unisex | 0.24 | 0.13 | 54% |
| PAMPERS EASY UPS—Unisex | 0.14 | 0.12 | 86% |
| New & Improved PAMPERS EASY UPS—Unisex | 0.21 | 0.10 | 48% |
| PARAGON White Cloud—Boy | 0.35 | 0.22 | 63% |
| PARAGON White Cloud—Girl | 0.33 | 0.19 | 58% |
| MERRIES Slender Fit—Unisex | 0.20 | 0.14 | 70% |
| HIUGGIES LITTLE SWIMMERS Disposable Swimpants—Unisex | 16.22 | 16.87 | 104% |
| LUVS SPLASHWEAR—Unisex | 14.87 | 13.90 | 93% |
| Early Trainer Vinyl & Cloth Training Pant—Unisex (size 4) | 20.14 | 20.89 | 104% |
| GERBER Cloth Training Pants—Unisex (size 4) | 13.62 | 13.07 | 96% |

Samples 1–5 were the only products that exhibited pooling, along with the ability to lock up the fluid after time. Thus, a wearer can experience the sloshing initially, but over time the wetness on the child's skin decreases and the locked up fluid does not spill out of the garment when the garment is being removed from the wearer.

Example 3

Fluid Distribution

In this example, fluid distribution of an 80 ml insult deposited onto a target area of each of the products in Table 1 was determined using the Cradle Test. Results are shown in Table 6.

TABLE 6

Fluid Distribution

| Product | Pad Length Utilization (%) |
|---|---|
| Sample 1 (Boy) | 76 |
| Sample 2 (Girl) | 78 |
| Sample 3 (Boy) | 75 |
| Sample 4 (Boy) | 76 |
| Sample 5 (Boy) | 80 |
| Kao Torepants—Unisex | 69 |
| Unicharm Torepan Man—Boy | 70 |
| Unicharm Torepan Man—Girl | 75 |
| HUGGIES PULL-UPS Disposable Training Pants, commercially available between about April 2002 and September 2002—Boy | 53 |
| HUGGIES PULL-UPS Disposable Training Pants, commercially available between about April 2002 and September 2002—Girl | 55 |
| HUGGIES PULL-UPS Disposable Training Pants, commercially available between about July 2001 and April 2002—Boy | 51 |
| HUGGIES Supreme Disposable Diapers—Unisex | 41 |
| HUGGIES Ultratrim Disposable Diapers—Unisex | 44 |
| PAMPERS EASY UPS—Unisex | 39 |
| New & Improved PAMPERS EASY UPS—Unisex | 43 |

TABLE 6-continued

Fluid Distribution

| Product | Pad Length Utilization (%) |
|---|---|
| PARAGON White Cloud—Boy | 49 |
| PARAGON White Cloud—Girl | 48 |
| MERRIES Slender Fit—Unisex | 55 |
| HUGGIES LITTLE SWIMMERS Disposable Swimpants—Unisex | 94 |
| LUVS SPLASHWEAR—Unisex | 87 |
| Early Trainer Vinyl & Cloth Training Pant—Unisex (size 4) | 79 |
| GERBER Cloth Training Pants—Unisex (size 4) | 46 |

Samples 1–5 use at least 75% of the pad length, which means that wetness along at least 75% of the pad length may come in contact with the wearer's skin, thereby allowing the wearer to feel the wetness.

Example 4

Absorbent Capacity

In this example, the absorbent capacity of each of the products in Table 1 was determined using the Modified Saturated Capacity Test. Results are shown in Table 7.

TABLE 7

Absorbent Capacity

| Product | Absorbent Capacity (grams) |
|---|---|
| Sample 1 (Boy) | 160 |
| Sample 2 (Girl) | 173 |
| Sample 3 (Boy) | 168 |
| Sample 4 (Boy) | 163 |
| Sample 5 (Boy) | 171 |
| Kao Torepants—Unisex | 250 |
| Unicharm Torepan Man—Boy | 133 |
| Unicharm Torepan Man—Girl | 125 |
| HUGGIES PULL-UPS Disposable Training Pants, commercially available between about April 2002 and September 2002—Boy | 419 |
| HUGGIES PULL-UPS Disposable Training Pants, commercially available between about April 2002 and September 2002—Girl | 403 |
| HUGGIES PULL-UPS Disposable Training Pants, commercially available between about July 2001 and April 2002—Boy | 510 |
| HUGGIES Supreme Disposable Diapers—Unisex | 525 |
| HUGGIES Ultratrim Disposable Diapers—Unisex | 561 |
| PAMPERS EASY UPS—Unisex | 520 |
| New & Improved PAMPERS EASY UPS—Unisex | 495 |
| PARAGON White Cloud—Boy | 449 |
| PARAGON White Cloud—Girl | 482 |
| MERRIES Slender Fit—Unisex | 562 |
| HUGGIES LITTLE SWIMMERS Disposable Swimpants—Unisex | 91 |
| LUVS SPLASHWEAR—Unisex | 109 |
| Early Trainer Vinyl & Cloth Training Pant—Unisex (size 4) | 190 |
| GERBER Cloth Training Pants—Unisex (size 4) | 188 |
| HANES Cloth Underwear—Boy (size 4) | 79 |
| HANES Cloth Underwear—Girl (size 4) | 58 |

Bulk and Density Testing

A region of the absorbent pad to be tested is placed under a 0.2 psi weight, and the bulk of the absorbent in this region is recorded. The area under compression should be larger than a 2-inch by 2-inch (5.08-cm by 5.08-cm) square. A suitable tester for absorbent bulk is a Starret-type bulk tester equipped with a 3-inch diameter brass foot that applies a weight of 0.2 psi. The area under compression is marked around the perimeter of the weight while the weight is in place. The weight is removed, and a 2-inch by 2-inch square is cut out from within the outlined region, such as by a die cut. Any tissue present on the absorbent pad is removed, and the square is weighed. The density is determined by the following calculation: density=(mass of absorbent in grams)/[$(5.08 \text{ cm})^2 \times$(bulk in cm)].

Modified Saturated Capacity Test Method

Figure 5:
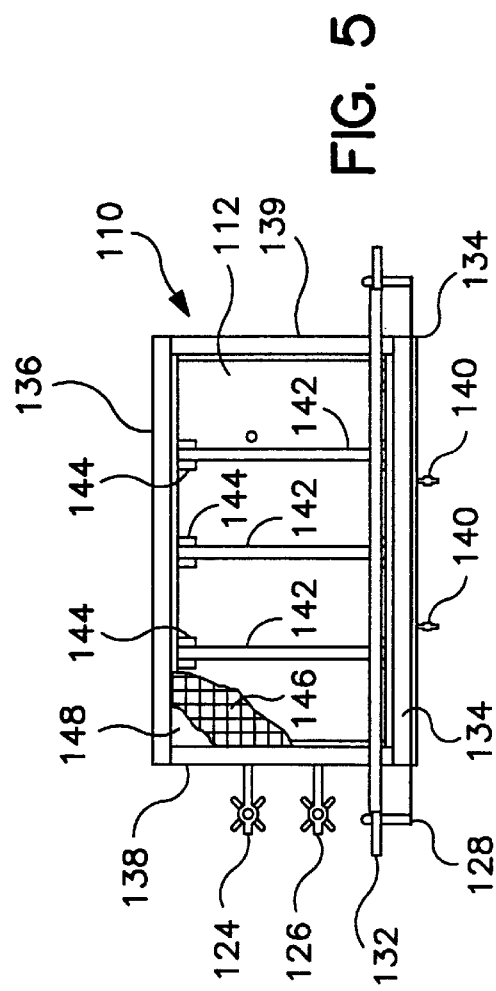
FIG. 5 representatively shows a partially cut away top view of a saturated capacity tester.
Figure 7:
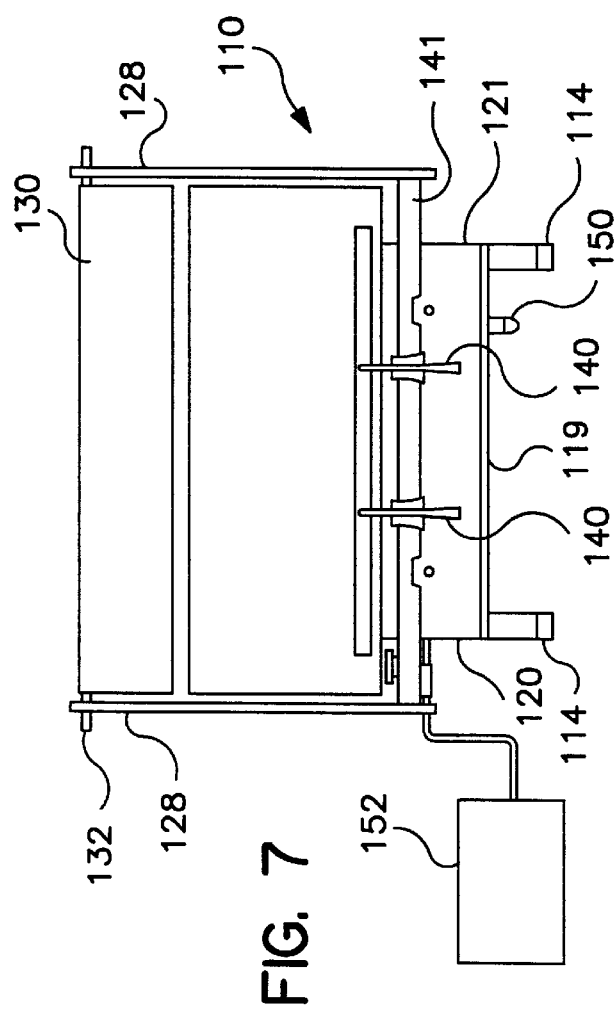
FIG. 7 representatively shows a rear view of a saturated capacity tester.
Figure 6:
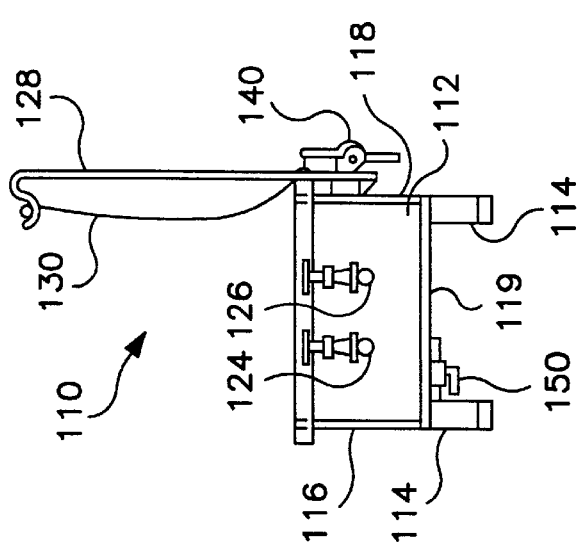
FIG. 6 representatively shows a side view of a saturated capacity tester.

Saturated Capacity is determined using a Saturated Capacity (SAT CAP) tester with a Magnahelic vacuum gage and a latex dam. Referring to FIGS. 5–7, a Saturated Capacity tester vacuum apparatus 110 comprises a vacuum chamber 112 supported on four leg members 114. The vacuum chamber 112 includes a front wall member 116, a rear wall member 118 and two side walls 120 and 121. The wall members are about 0.5 inch thick, and are constructed and arranged to provide a chamber having outside dimensions measuring 23.5 inches in length, 14 inches in width and 8 inches in depth.

A vacuum pump (not shown) operably connects with the vacuum chamber 112 through an appropriate vacuum line conduit and a vacuum valve 124. In addition, a suitable air bleed line connects into the vacuum chamber 112 through an air bleed valve 126. A hanger assembly 128 is suitably mounted on the rear wall 118 and is configured with S-curved ends to provide a convenient resting place for supporting a latex dam sheet 130 in a convenient position away from the top of the vacuum apparatus 110. A suitable hanger assembly can be constructed from 0.25 inch diameter stainless steel rod. The latex sheet 130 is looped around a dowel member 132 to facilitate grasping and to allow a convenient movement and positioning of the latex sheet 130. In the illustrated position, the dowel member 132 is shown supported in a hanger assembly 128 to position the latex sheet 130 in an open position away from the top of the vacuum chamber 112.

A bottom edge of the latex sheet 130 is clamped against a rear edge support member 134 with suitable securing means, such as toggle clamps 140. The toggle clamps are mounted on the rear wall member 118 with suitable spacers 141 which provide an appropriate orientation and alignment of the toggle clamps 140 for the desired operation. Three support shafts 142 are 0.75 inches in diameter and are removably mounted within the vacuum chamber 112 by means of support brackets 144. The support brackets 144 are generally equally spaced along the front wall member 116 and the rear wall member 118 and arranged in cooperating pairs. In addition, the support brackets 144 are constructed and arranged to suitably position the uppermost portions of the support shafts 142 flush with the top of the front, rear and side wall members of the vacuum chamber 112. Thus, the support shafts 142 are positioned substantially parallel with one another and are generally aligned with the side wall members 120 and 121. In addition to the rear edge support member 134, the apparatus 110 includes a front support member 136 and two side support members 138 and 139. Each side support member measures about 1 inch in width and about 1.25 inches in height. The lengths of the support members are constructed to suitably surround the periphery of the open top edges of the vacuum chamber 112, and are positioned to protrude above the top edges of the chamber wall members by a distance of about 0.5 inches.

A layer of egg crating type material 146 is positioned on top of the support shafts 142 and the top edges of the wall members of the vacuum chamber 112. The egg crate material extends over a generally rectangular area measuring 23.5 inches by 14 inches, and has a depth measurement of about 0.38 inches. The individual cells of the egg crating structure measure about 0.5 inch square, and the thin sheet material comprising the egg crating is composed of a suitable material, such as polystyrene. For example, the egg crating material can be McMaster Supply Catalog No. 162 4K 14, translucent diffuser panel material. A layer of 0.19 mesh nylon screening 148, which measures 23.5 inches by 14 inches, is placed on top of egg crating material 146.

A suitable drain line and a drain valve 150 connect to bottom plate member 119 of the vacuum chamber 112 to provide a convenient mechanism for draining liquids from the vacuum chamber 112. The various wall members and support members of tester apparatus 110 may be composed of a suitable noncorroding, moisture-resistant material, such as polycarbonate plastic. The various assembly joints may be affixed by solvent welding, and the finished assembly of the tester is constructed to be watertight. A vacuum gauge 152 operably connects through a conduit into the vacuum chamber 112. A suitable pressure gauge is a Magnahelic differential gauge capable of measuring a vacuum of 0–100 inches of water, such as a No. 2100 gauge available from Dwyer Instrument Incorporated.

The dry product or other absorbent structure is weighed and then placed in excess 0.9% saline solution and allowed to soak for 20 minutes. After the 20 minute soak time, the absorbent structure is placed on the egg crate material and mesh nylon screening of the Saturated Capacity tester. The latex sheet is placed over the absorbent structure(s) and the entire egg crate grid so that the latex sheet creates a seal when a vacuum is drawn on the tester. A vacuum of 0.5 pounds per square inch (psi) is held in the Saturated Capacity tester for five minutes. The vacuum creates a pressure on the absorbent structure(s), causing drainage of some liquid. After five minutes at 0.5 psi vacuum, the latex sheet is rolled back and the absorbent structure(s) are weighed to generate a wet weight.

The overall capacity of each absorbent structure is determined by subtracting the dry weight of each absorbent from the wet weight of that absorbent determined at this point in the procedure. The 0.5 psi SAT CAP or SAT CAP of the absorbent structure is determined by the following formula:

SAT CAP=(wet weight−dry weight)/dry weight;

wherein the SAT CAP value has units of grams fluid/gram absorbent. For both overall capacity and SAT CAP, a minimum of four specimens of each sample should be tested and the results averaged. If the absorbent structure has low integrity or disintegrates during the soak or transfer procedures, the absorbent structure can be wrapped in a containment material such as paper toweling, for example Hi-Dri® paper towels manufactured by Kimberly-Clark Corporation, Neenah, Wis., U.S.A. The absorbent structure can be tested with the overwrap in place and the capacity of the overwrap can be independently determined and subtracted from the wet weight of the total wrapped absorbent structure to obtain a wet absorbent weight.

Cradle Test Method

Figure 4A:
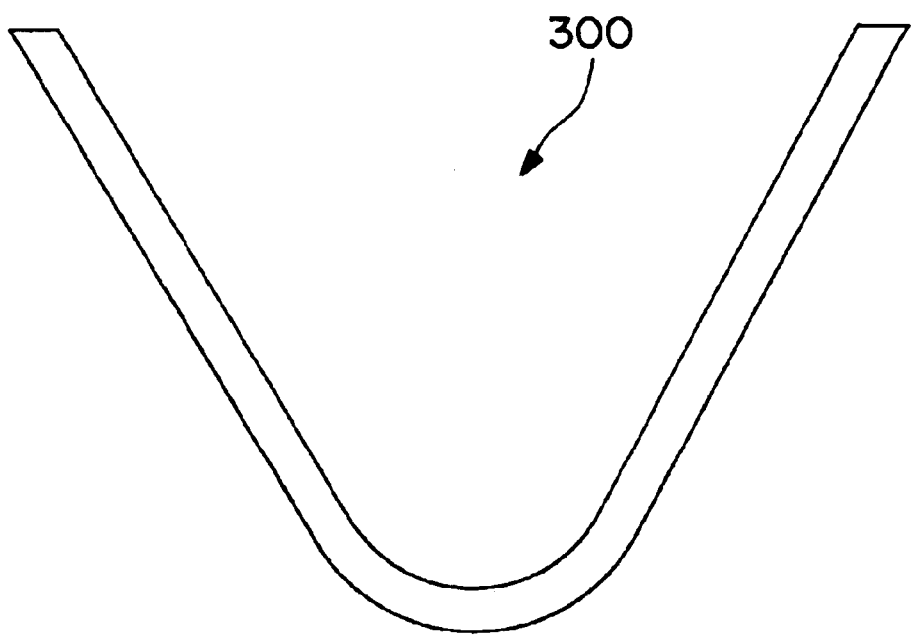
FIG. 4a representatively shows an unslotted cradle suitable for use in a Cradle Test.
Figure 4B:
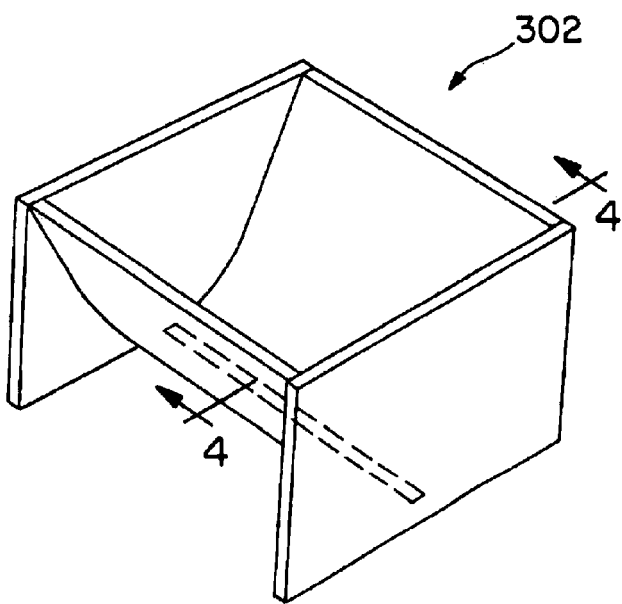
FIG. 4b representatively shows a slotted cradle suitable for use in a Cradle Test.
Figure 4C:
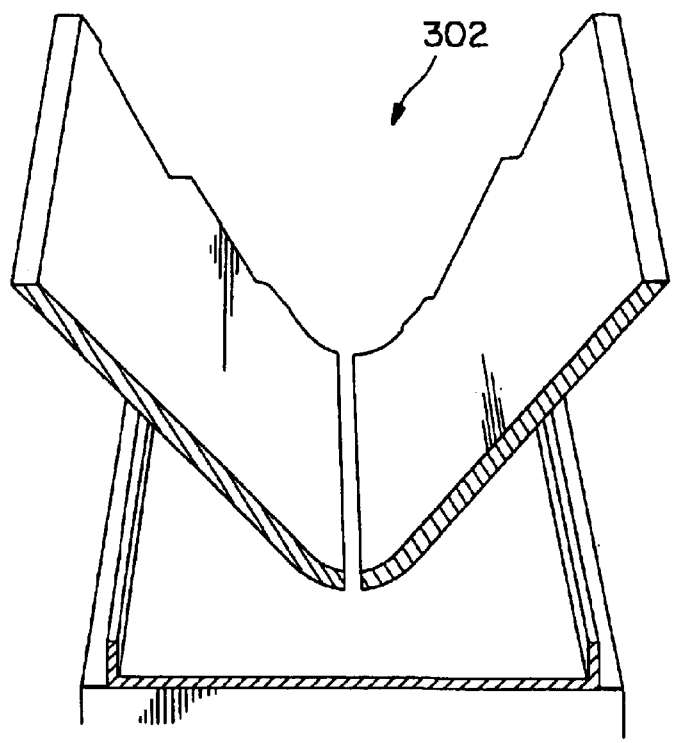
FIG. 4c representatively shows a cross-sectional view of the slotted cradle taken along line 4—4 of FIG. 4b.

The Cradle Test replicates real-life positioning of a garment on a wearer, and can be used to determine intake rates, flowback, and fluid distribution of a garment. This method uses an unslotted cradle 300, as shown in FIG. 4a, and a slotted cradle 302, as shown in FIGS. 4b and 4c, both made up of a water-resistant material such as acrylic plastic and simulating body curvature of a wearer.

The unslotted cradle has an overall length of 487 mm, an inside width of 315 mm and a height of 205 mm. The entire device is constructed of 6 mm thick plastic. A series of three acrylic partitions, running perpendicular to the length of the cradle, separate the body into four bays. Each bay is approximately 115 mm in width. The curvature of the cradle is formed by a 60-degree angle.

The slotted cradle has an overall length of 350 mm, a side-to-side width of 355 mm and a height of 365 mm (including about 50 mm height below the slot). Material used in the construction varies in thickness from 6 mm to 12 mm. The cradle has a 6 mm wide slot at the lowest point which runs the length of the cradle. The curvature of the cradle is formed by a 60-degree angle, and the entire cradle assembly can be rotated via two lockdown knobs.

1. Product Preparation

A. Cut open the three-dimensional pant style products at the sides or side seams to make the product two-dimensional.

B. Do not snip the leg and containment flap elastics.

C. Weigh the product to the nearest 0.01 gram value and record the value.

D. Measure the pad length (using a light board) to the nearest 1 mm value and record the value.

E. Mark the insult area with a "+" (using the light board) at 162 mm from the front waist edge of the product to the nearest 1 mm value. Center the measurement in the cross direction. Do not measure from the front edge of the pad.

F. Measure the product length and mark the center with a "_" to align with the bottom of the cradle. This will aid in correctly positioning the product in the cradle.

2. Product Testing (Test Fluid=0.9 w/v % Saline Solution)

A. Verify that the pump delivers the required test fluid amount for the insult +/−0.5 ml. The flow rate should be set at approximately 11–14 ml/second.

i. Test fluid amount will be specified as 40 ml or 80 ml.

B. For the slotted cradle, place a capture container of known weight under the cradle slot to catch the fluid overflow. Measure the weight of the capture container to the nearest 0.01 grams.

i. Note: low capacity products without flaps (i.e., cloth underwear, cloth training pants, vinyl/cloth training pants) will be prone to overflow.

C. Weigh another set of blotter papers for flowback to the nearest 0.01 gram.

D. Position the specimen, liner/inside side up, with the "pre-marked" center of the product lined up with and touching the lowest point in the cradle. The entire length of the outer cover/outside of the product should make contact with the cradle. Clip or otherwise attach the product to the cradle at the front and back waist edges to keep it in place. Gently pull on the front/back waist of the specimen to smooth out any wrinkles or creases in the product.

i. For the cradle testing, all product codes will be insulted at a point 162 mm from the front waist edge of the product.

E. Hold the nozzle above the target area and perpendicular to the specimen. The bottom of the nozzle should be within 5 to 10 mm from the specimen.

F. Initiate the insult and start the stopwatch when the testing fluid leaves the nozzle. As soon as the insult is complete, move the nozzle aside to observe the testing fluid.

G. Stop the stopwatch immediately when the testing fluid is not visible on the specimen surface.
  i. Record the intake time to the nearest 0.01 second.
    a. If the fluid overflows into the capture container, the intake time will be recorded when no more fluid is visible on the surface. Therefore, intake time could equal the time it takes to "pour" the entire insult onto the product.
    b. Observe whether the overflow occurred during or after the insult.
    c. Some products may have difficulty absorbing the entire insult, but may not overflow.
      1. If the insult absorbs completely prior to 30 minutes, then record the time as such.
      2. If the insult fails to absorb after 30 minutes, then record the time as 30 minutes +.
H. Once the insult is absorbed or the 30 minute+time has elapsed, immediately set the timer for the specified wait time. Leave the specimen in the cradle for the entire wait time.
  i. For those products that do not overflow and do not absorb the insult after 30 minutes, leave any excess or loose fluid in the pant for the remainder of the test (including for the flowback measurement).
    a. Start the wait times (1 and 15 minutes, respectively) at the end of the intake time specified above, and measure fluid distribution (30 seconds and 10 minutes, respectively) and flowback (1 and 15 minutes, respectively).
I. During the wait time, measure and record the overflow to the nearest 0.01 grams.
J. After a designated portion of the specified wait time has elapsed, mark the furthest distance wicked by the fluid at the front and back of the product. This distance can be measured and recorded after the test is complete.
  i. For a 1 minute wait, mark the distance at 30 seconds.
  ii. For a 15 minute wait, mark the distance at 10 minutes.
K. Just prior to the end of the wait period (while the specimen is still in the cradle), snip the containment flap elastics on both sides of the product at approximately 1-inch intervals.
L. At the end of the wait period, immediately transfer the specimen from the cradle to the Saturated Capacity tester. Keep the specimen cradled during the transfer and then place flat (horizontal) on the Saturated Capacity tester box with the liner/inside side up. Center the specimen on the Saturated Capacity tester.
M. Place the pre-weighed blotter papers designated for flowback onto the specimen's absorbent side. Center the blotter paper over the wet area.
N. Cover the specimen and blotter papers with the latex rubber sheet and press the start button on the vacuum control box.
O. Maintain 0.5+/−0.04 psi on the Saturated Capacity tester for 2 minutes. After the elapsed time, lift the latex rubber sheet to release the pressure from the Saturated Capacity tester.
P. Immediately remove the blotter papers, weigh to the nearest 0.01 gram, and record the value of flowback.
Q. Remove the specimen from the Saturated Capacity tester box and attach to a plastic board in the elongated position. Measure the greatest distance of fluid wicked to the nearest 1 mm (marked during the wait time before flowback) and record the value for fluid distribution.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. A disposable absorbent pant, comprising:
  a chassis defining a waist opening and first and second leg openings;
  the chassis including an outer cover, a body side liner at least partially bonded to the outer cover, and an absorbent pad positioned between the outer cover and the body side liner;
  the disposable absorbent pant having an intake rate for a 40 milliliter insult of at least 7 seconds, an intake rate for an 80 milliliter insult of at least 45 seconds, a final flowback of a 40 milliliter insult of less than 35% of an initial flowback of the 40 milliliter insult, a final flowback of an 80 milliliter insult of less than 60% of an initial flowback of the 80 milliliter insult, and a fluid distribution of an 80 milliliter insult of at least 60%, each according to a Cradle Test.

2. The disposable absorbent pant of claim 1, wherein the disposable absorbent pant has an absorbent capacity of between about 40 grams and about 300 grams.

3. The disposable absorbent pant of claim 1, wherein the disposable absorbent pant has an absorbent capacity of between about 40 grams and about 300 grams.

4. The disposable absorbent pant of claim 1, wherein the disposable absorbent pant has an absorbent capacity of between about 50 grams and about 150 grams.

5. The disposable absorbent pant of claim 1, wherein the absorbent pad has a thickness of less than about 2 millimeters.

6. The disposable absorbent pant of claim 1, wherein the outer cover, the body side liner, the absorbent pad, and any additional layers between the outer cover and the body side liner, have a combined thickness of less than about 3 millimeters.

7. The disposable absorbent pant of claim 1, further comprising at least one of the group consisting of a pair of containment flaps, a pair of leg elastics, a pair of leg cuffs, and combinations thereof, adjacent the first and second leg openings.

8. A disposable absorbent pant, comprising:
  a chassis defining a waist opening and first and second leg openings;
  the chassis including an outer cover, a body side liner at least partially bonded to the outer cover, and an absorbent pad positioned between the outer cover and the body side liner;
  the disposable absorbent pant having an absorbent capacity of between about 30 grams and about 400 grams; and
  the disposable absorbent pant having an intake rate for a 40 milliliter insult of at least 7 seconds, and an intake rate for an 80 milliliter insult of at least 45 seconds, each according to a Cradle Test.

9. The disposable absorbent pant of claim 8, wherein the intake rate for a 40 milliliter insult is at least 12 seconds, according to a Cradle Test.

10. The disposable absorbent pant of claim 8, wherein the intake rate for a 40 milliliter insult is at least 16 seconds, according to a Cradle Test.

11. The disposable absorbent pant of claim 8, wherein the intake rate for an 80 milliliter insult is at least 65 seconds, according to a Cradle Test.

12. The disposable absorbent pant of claim 8, wherein the intake rate for an 80 milliliter insult is at least 80 seconds, according to a Cradle Test.

13. The disposable absorbent pant of claim 8, wherein the disposable absorbent pant has a final flowback of a 40 milliliter insult of less than 35% of an initial flowback of the 40 milliliter insult, according to a Cradle Test.

14. The disposable absorbent pant of claim 8, wherein the disposable absorbent pant has a final flowback of a 40 milliliter insult of less than 30% of an initial flowback of the 40 milliliter insult, according to a Cradle Test.

15. The disposable absorbent pant of claim 8, wherein the disposable absorbent pant has a final flowback of a 40 milliliter insult of less than 25% of an initial flowback of the 40 milliliter insult, according to a Cradle Test.

16. The disposable absorbent pant of claim 8, wherein the disposable absorbent pant has a final flowback of an 80 milliliter insult of less than 60% of an initial flowback of the 80 milliliter insult, according to a Cradle Test.

17. The disposable absorbent pant of claim 8, wherein the disposable absorbent pant has a final flowback of an 80 milliliter insult of less than 50% of an initial flowback of the 80 milliliter insult, according to a Cradle Test.

18. The disposable absorbent pant of claim 8, wherein the disposable absorbent pant has a final flowback of an 80 milliliter insult of less than 45% of an initial flowback of the 80 milliliter insult, according to a Cradle Test.

19. The disposable absorbent pant of claim 8, wherein the disposable absorbent pant has a fluid distribution of an 80 milliliter insult of at least 60%, according to a Cradle Test.

20. The disposable absorbent pant of claim 8, wherein the disposable absorbent pant has a fluid distribution of an 80 milliliter insult of at least 65%, according to a Cradle Test.

21. The disposable absorbent pant of claim 8, wherein the disposable absorbent pant has a fluid distribution of an 80 milliliter insult of at least 70%, according to a Cradle Test.

22. The disposable absorbent pant of claim 8, wherein the absorbent capacity is between about 40 grams and about 300 grams.

23. The disposable absorbent pant of claim 8, wherein the absorbent capacity is between about 50 grams and about 150 grams.

24. The disposable absorbent pant of claim 8, wherein the absorbent pad has a thickness of less than about 2 millimeters.

25. The disposable absorbent pant of claim 8, wherein the outer cover, the body side liner, the absorbent pad, and any additional layers between the outer cover and the body side liner, have a combined thickness of less than about 3 millimeters.

26. The disposable absorbent pant of claim 8, further comprising at least one of the group consisting of a pair of containment flaps, a pair of leg elastics, a pair of leg cuffs, and combinations thereof, adjacent the first and second leg openings.

27. A disposable absorbent pant, comprising:
a chassis defining a waist opening and first and second leg openings;
the chassis including an outer cover, a body side liner at least partially bonded to the outer cover, and an absorbent pad positioned between the outer cover and the body side liner;
the disposable absorbent pant having an absorbent capacity of between about 30 grams and about 400 grams; and
the disposable absorbent pant having a final flowback of a 40 milliliter insult of less than 35% of an initial flowback of the 40 milliliter insult, and a final flowback of an 80 milliliter insult of less than 60% of an initial flowback of the 80 milliliter insult, each according to a Cradle Test.

28. The disposable absorbent pant of claim 27, wherein the disposable absorbent pant has a final flowback of a 40 milliliter insult of less than 30% of an initial flowback of the 40 milliliter insult, according to a Cradle Test.

29. The disposable absorbent pant of claim 27, wherein the disposable absorbent pant has a final flowback of a 40 milliliter insult of less than 25% of an initial flowback of the 40 milliliter insult, according to a Cradle Test.

30. The disposable absorbent pant of claim 27, wherein the disposable absorbent pant has a final flowback of an 80 milliliter insult of less than 50% of an initial flowback of the 80 milliliter insult, according to a Cradle Test.

31. The disposable absorbent pant of claim 27, wherein the disposable absorbent pant has a final flowback of an 80 milliliter insult of less than 45% of an initial flowback of the 80 milliliter insult, according to a Cradle Test.

32. The disposable absorbent pant of claim 27, wherein the disposable absorbent pant has a fluid distribution of an 80 milliliter insult of at least 60%, according to a Cradle Test.

33. The disposable absorbent pant of claim 27, wherein the disposable absorbent pant has a fluid distribution of an 80 milliliter insult of at least 65%, according to a Cradle Test.

34. The disposable absorbent pant of claim 27, wherein the disposable absorbent pant has a fluid distribution of an 80 milliliter insult of at least 70%, according to a Cradle Test.

35. The disposable absorbent pant of claim 27, wherein the absorbent capacity is between about 40 grams and about 300 grams.

36. The disposable absorbent pant of claim 27, wherein the absorbent capacity is between about 50 grams and about 150 grams.

37. The disposable absorbent pant of claim 27, wherein the absorbent pad has a thickness of less than about 2 millimeters.

38. The disposable absorbent pant of claim 27, wherein the outer cover, the body side liner, the absorbent pad, and any additional layers between the outer cover and the body side liner, have a combined thickness of less than about 3 millimeters.

39. The disposable absorbent pant of claim 27, further comprising at least one of the group consisting of a pair of containment flaps, a pair of leg elastics, a pair of leg cuffs, and combinations thereof, adjacent the first and second leg openings.

40. A disposable absorbent pant, comprising:
a chassis defining a waist opening and first and second leg openings;
the chassis including an outer cover, a body side liner at least partially bonded to the outer cover, and an absorbent pad positioned between the outer cover and the body side liner;
the disposable absorbent pant having an absorbent capacity of between about 30 grams and about 400 grams; and
the disposable absorbent pant having a fluid distribution of an 80 milliliter insult of at least 60%, according to a Cradle Test.

41. The disposable absorbent pant of claim 40, wherein the disposable absorbent pant has a fluid distribution of an 80 milliliter insult of at least 65%, according to a Cradle Test.

42. The disposable absorbent pant of claim 40, wherein the disposable absorbent pant has a fluid distribution of an 80 milliliter insult of at least 70%, according to a Cradle Test.

43. The disposable absorbent pant of claim 40, wherein the absorbent capacity is between about 40 grams and about 300 grams.

44. The disposable absorbent pant of claim 40, wherein the absorbent capacity is between about 50 grams and about 150 grams.

45. The disposable absorbent pant of claim 40, wherein the absorbent pad has a thickness of less than about 2 millimeters.

46. The disposable absorbent pant of claim 40, wherein the outer cover, the body side liner, the absorbent pad, and any additional layers between the outer cover and the body side liner, have a combined thickness of less than about 3 millimeters.

47. The disposable absorbent pant of claim 40, further comprising at least one of the group consisting of a pair of containment flaps, a pair of leg elastics, a pair of leg cuffs, and combinations thereof, adjacent the first and second leg openings.

48. A method of toilet training a child, comprising:
applying a disposable absorbent pant to the child, wherein the disposable absorbent pant has an intake rate for a 40 milliliter insult of at least 7 seconds, an intake rate for an 80 milliliter insult of at least 45 seconds, a final flowback of a 40 milliliter insult of less than 35% of an initial flowback of the 40 milliliter insult, a final flowback of an 80 milliliter insult of less than 60% of an initial flowback of the 80 milliliter insult, and a fluid distribution of an 80 milliliter insult of at least 60%, each according to a Cradle Test.

* * * * *

UNITED STATES PATENT AND TRADEMARK OFFICE
CERTIFICATE OF CORRECTION

PATENT NO. : 6,727,404 B2
DATED : April 27, 2004
INVENTOR(S) : Ruman et al.

It is certified that error appears in the above-identified patent and that said Letters Patent is hereby corrected as shown below:

<u>Title page,</u>
Item [74], Inventors, change "Marcille Faye Ruman, Neenah, WI" to -- Marcille Faye Ruman, Oshkosh, WI --

Signed and Sealed this

Twenty-ninth Day of June, 2004

JON W. DUDAS
*Acting Director of the United States Patent and Trademark Office*